(12) United States Patent
Phinney et al.

(10) Patent No.: US 6,511,064 B1
(45) Date of Patent: Jan. 28, 2003

(54) METHOD AND APPARATUS FOR MULTIPLE DOCUMENT DETECTION USING ULTRASONIC PHASE SHIFT AMPLITUDE

(75) Inventors: Daniel P. Phinney, Rochester, NY (US); David M. Pultorak, Rochester, NY (US); Albert H. Titus, Batavia, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/552,064

(22) Filed: Apr. 19, 2000

(51) Int. Cl.$^7$ .............................. B65H 7/12; G01S 3/80
(52) U.S. Cl. ................... 271/262; 271/258.01; 367/125
(58) Field of Search .......................... 271/258.01, 262, 271/263; 367/124, 125, 127

(56) References Cited

U.S. PATENT DOCUMENTS

| | | | | |
|---|---|---|---|---|
| 4,066,969 A | | 1/1978 | Pearce et al. ............ 271/263 X |
| 4,368,438 A | * | 1/1983 | Stienstra ...................... 331/14 |
| 5,023,846 A | * | 6/1991 | Busch-Sorensen .......... 367/127 |
| 6,145,376 A | * | 11/2000 | Elgee ..................... 271/9.06 X |
| 6,212,130 B1 | * | 4/2001 | Brazeal, Jr. et al. .... 271/258.01 X |

* cited by examiner

*Primary Examiner*—Tuan N. Nguyen
(74) *Attorney, Agent, or Firm*—Nelson Adrian Blish

(57) ABSTRACT

According to one aspect of the present invention an apparatus for multiple document detection includes an ultrasonic transmitter (14) for transmitting an ultrasonic signal (16). An ultrasonic receiver (20) receives the ultrasonic signal (17), after it passes through the at least one of the multiple documents (18). A phase comparator (24) compares the transmitted ultrasonic signal (16) and the received ultrasonic signal (17), and an amplitude measurement circuit (26) compares the received ultrasonic signal (17) to a reference. A microprocessor (32) compares an information signal (28) from the phase comparator (24) and an information signal (30) from the amplitude measurement circuit (26) to a predetermined threshold to determine if multiple documents are present.

19 Claims, 2 Drawing Sheets

METHOD AND APPARATUS FOR MULTIPLE DOCUMENT DETECTION USING ULTRASONIC PHASE SHIFT AMPLITUDE

FIELD OF THE INVENTION

This invention relates in general to document transports and in particular, to ultrasonic detectors for multiple document feeds.

BACKGROUND OF THE INVENTION

Scanners and copiers use document feeders to transport documents into a machine. Mechanisms used for the transportation of documents, including paper or sheets of other material, have the capacity to accidentally pick up more than one document fed from a stack of documents. It is necessary to determine when more than one document is pulled into a document transport since multiple documents may jam the transport or prevent processing some documents.

There are two general methods for multiple document detection, contact and non-contact. The contact methods include measurement of small thickness changes with a contact foot or sensing arm that is in contact with the documents as they pass through the document transport. The contact foot is connected to a Linear Voltage Differential Transducer (LVDT), or a magnet, which is sensed by a Hall Effect Sensor. These sensors can detect changes in thickness of less than 1 $\mu$m ($10^{-6}$ m).

The major disadvantage to the contact method is that anything in contact with moving paper, especially thin paper or ripped paper, can cause a malfunction such as a paper jam. The contact method also requires calibration using the maximum thickness document that will be fed through the document transport. When a thickness is measured which is above the calibration value plus a threshold, typically 30%, it is determined to be a multiple document feed. This method, however, will only work when documents having a uniform thickness are processed. Using a wheel on the end of the contact foot can reduce the chances of paper jam, however, the variations in the diameter of this wheel, due to the nonconformity's in manufacturing, must be taken into account during the measurements, which further complicates the measurement.

The primary non-contact method for multiple document detection sends ultrasound signals through the document stream to determine if more than one document is present. Sending ultrasound through paper results in attenuation of the ultrasound signal. It is possible to determine the presence of multiple documents by the change in attenuation of the signal received. This method is independent of the thickness of the individual documents and is made without making contact with these documents.

A typical contact document scanner is able to detect about 94% of the test multiple documents. An attenuation detector that was tested was only able to detect about 86% of these same test multiple documents, thus there is an opportunity for improvement using ultrasound detection.

For detecting multiple documents by attenuation methods, the performance improves as higher frequency transmitters and receivers are used. Unfortunately, the cost of these components also increases with frequency. There is also a limited range of paper thicknesses that can be properly detected. Therefore, the attenuation method alone is not suitable for multiple document detection.

The phase shift of ultrasound signal passing through documents has been used to detect multiple document feeds. See U.S. Pat. No. 4,066,969 which is herein incorporated by reference. Unfortunately, using phase shift is not reliable since multiple documents may cause phase shifts greater than 360 degrees. For detecting multiple documents by phase methods, the performance decreases at higher frequencies because the wavelength is shorter and the method becomes more sensitive to signal variations.

SUMMARY OF THE INVENTION

It is an object of the present invention to provide an improved method and apparatus for multiple document detection, which is both accurate and relatively inexpensive.

An apparatus for multiple document detection in accordance with an embodiment of the present invention includes a signaling system and an analyzer. The signaling system transmits a signal to and receives the signal from a document feed which comprises one or more documents. The analyzer determines if the document feed comprises two or more of the documents in response to a phase shift and an amplitude change between the transmitted signal and the received signal.

A method for determining the presence of multiple documents in accordance with another embodiment of the present invention includes the following steps. An ultrasonic signal is transmitted through a document feed comprising one or more documents. The ultrasonic signal is received after it has passed through the document feed. A phase of the transmitted signal and a phase of the received signal are compared to provide a first information signal. An amplitude of the transmitted signal and an amplitude of the received signal are compared to provide a second information signal. The first and second information signals are analyzed to determine if the document feed comprises two or more of the documents.

An apparatus in accordance with another embodiment of the present invention includes a document processing system and a multiple document detection system. The document transports system supplies at least one document feed comprising one or more documents to the document processing system. The multiple document detection system determines if the document feed comprises two or more of the documents based on a phase shift and an amplitude change between a signal transmitted to and received from the document feed.

This invention uses both phase shift and amplitude variation of ultrasound passed through a document stream to determine the presence of multiple documents. By using both phase and the amplitude changes of the received ultrasound, the presence of multiple documents can be detected more reliably than is possible by using phase detection alone or amplitude detection alone.

Another advantage of the present invention is that the phase and amplitude changes in the received signal can be determined without physically contacting the paper. As a result, this invention will cause less document jams than direct contact methods.

Another advantage of this invention is that a transmitter and receiver that is used for phase shift and amplitude detection will be less expensive than for the same equipment used for detecting each separately. Additionally, the invention is able to use a low frequency transmitter and receiver, which is low cost, is less sensitive to variations in document thickness, and is able to detect a larger range of paper thickness.

The invention and its objects, various features, and advantages will become more apparent from the detailed description of the preferred embodiment presented below.

DETAILED DESCRIPTION OF THE INVENTION

Figure 1:
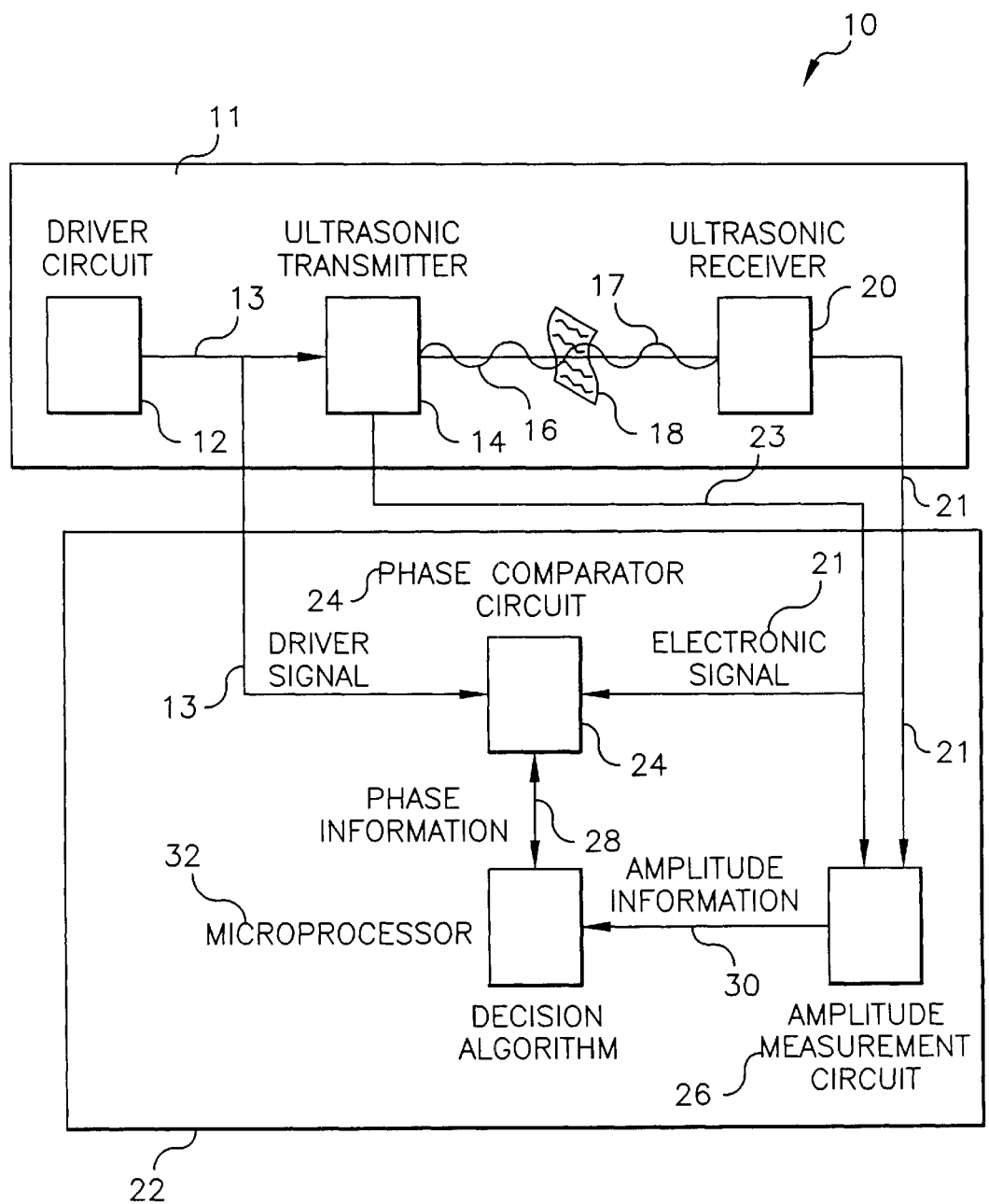
FIG. 1 is a block diagram of an ultrasonic detection circuit using phase shift and amplitude measurement in accordance with the present invention.

FIG. 1 shows an apparatus 10 for multiple document detection in accordance with one embodiment of the present invention. The apparatus includes a signaling system 11 and an analyzer 22. The signaling system transmits a signal to and receives the signal from a document feed which comprises one or more documents. The analyzer determines is the document feed comprises two or more of the documents in response to a phase shift and an amplitude change between the transmitted signal and the received signal. The present invention provides a number of advantages including providing an apparatus and a method for detecting the presence of multiple documents than has been possible with prior systems.

In this particular embodiment, the signaling system 11 includes an ultrasonic drive circuit 12, an ultrasonic transmitter 14, and an ultrasonic receiver 20, although other types of signaling systems with other components and operating in other frequency ranges or using other signals such as electromagnetics can be used. The ultrasonic drive circuit 12 provides a drive signal 13 to the ultrasonic transmitter 14. The ultrasonic transmitter 14 produces an ultrasonic signal 16 that passes through a document feed 18 and becomes an ultrasonic signal 17 with a different phase and amplitude which is then received by the ultrasonic receiver 20. Each document feed 18 comprises one or more documents. The ultrasonic receiver 20 converts the received ultrasonic signal 17 into an electrical signal 21. This resulting electrical signal 21 is conditioned and processed to interpret the amplitude and the phase information of the received ultrasonic signal 17.

In this particular embodiment, the analyzer 22 includes a phase comparator 24, an amplitude measurement circuit 26, and a microprocessor 32, although the other types of analyzers which can analyze phase and amplitude changes in a signal can be used. The electronic signal 21 is supplied to an input of the phase comparator 24 and of the amplitude measurement circuit 26. The resulting amplitude and phase information is used to make a determination of the presence of multiple documents in the document feed 18 as described in more detail below.

The ultrasonic signal 16 experiences a phase shift as it passes through each document feed 18 that is relatively independent of the thickness of the document or documents in the document feed 18. Instead, the phase shift experienced by the received ultrasonic signal 17 is approximately dependent on the number of documents in the document feed 18, because the interfaces between the different document or documents in the document feed 18 through which the ultrasound signal 16 passes, not the total thickness of the documents, effects the phase shift. The change in phase or phase difference in the received ultrasonic signal 17 is determined by comparing the electronic signal 21, which contains information based on the phase shift, and the drive signal 13, which is directly related to the phase of the transmitted ultrasonic signal 16. These signals are compared by the phase comparator 24. The phase comparator 24 provides an information signal 28 indicating the presence or absence of multiple documents based on the detected phase shift.

The amplitude of the received ultrasonic signal 17 is dependent on both the thickness of the documents and the number of documents in the document feed 18 that the transmitted ultrasonic signal 16 passes through. The amplitude of the received ultrasonic signal 17 which is represented by electrical signal 21 is compared against the amplitude of the transmitted ultrasonic signal 16 which is represented by electrical signal 23. A larger decrease in amplitude between the received and the transmitted ultrasonic signals 16 and 17 indicates the presence of multiple documents. The amplitude measurement circuit 26 provides an amplitude information signal 30 with an amplitude change dependent on the number of documents in the document feed 18 and to a lesser degree, the thickness of these documents in the document feed 18.

The information signal 28 from phase comparator 24 and the amplitude information signal 30 from the amplitude measurement circuit 26 are both fed to a microprocessor 32. The microprocessor 32 monitors information signal 28 and information signal 30 to determine if multiple documents are present. In the preferred embodiment both information signal 28 and information signal 30 must indicate the presence of multiple documents before the microprocessor 32 indicates a multiple document feed. In alternate embodiments microprocessor 32 may be programmed to indicate multiple documents in the document feed 18 if either the phase information signal 28 or the amplitude information signal 30 indicate multiple documents in the document feed 18. In yet another embodiment a weighting factor is assigned to each information signal 28 and 30 and a decision algorithm employed by the microprocessor 32 applies the weighting factor to each information signal 28 and 30 and then determines if multiple documents in the document feed 18 are present. In this particular embodiment, the decision algorithm is phase time W1 plus amplitude time W2 wherein W1 and W2 are predetermined values. Other algorithms could be used. The particular weighting factors used for each information signal 28 and 30 can vary as needed based on a variety of factors, such as the thickness of the documents in the document feed.

Use of both amplitude and phase from an ultrasonic signal transmitted through documents results in a more accurate detection system. Additionally, the system in accordance with the present invention requires no contact with the documents so the system is less likely to jam than contact systems.

In this particular embodiment, the transmitted signal 16 is an ultrasound signal, although other frequencies can be used. Ultrasonic is useful for detecting the presence or thickness of paper and other materials. As ultrasound, sound at ultrasonic frequencies passes through paper, it undergoes both a phase shift and an amplitude reduction. The present invention uses these changes to detect the presence of a document and to determine the number of documents present. From this information, it is possible to determine if overlapped documents or multiple documents are present.

Figure 2:
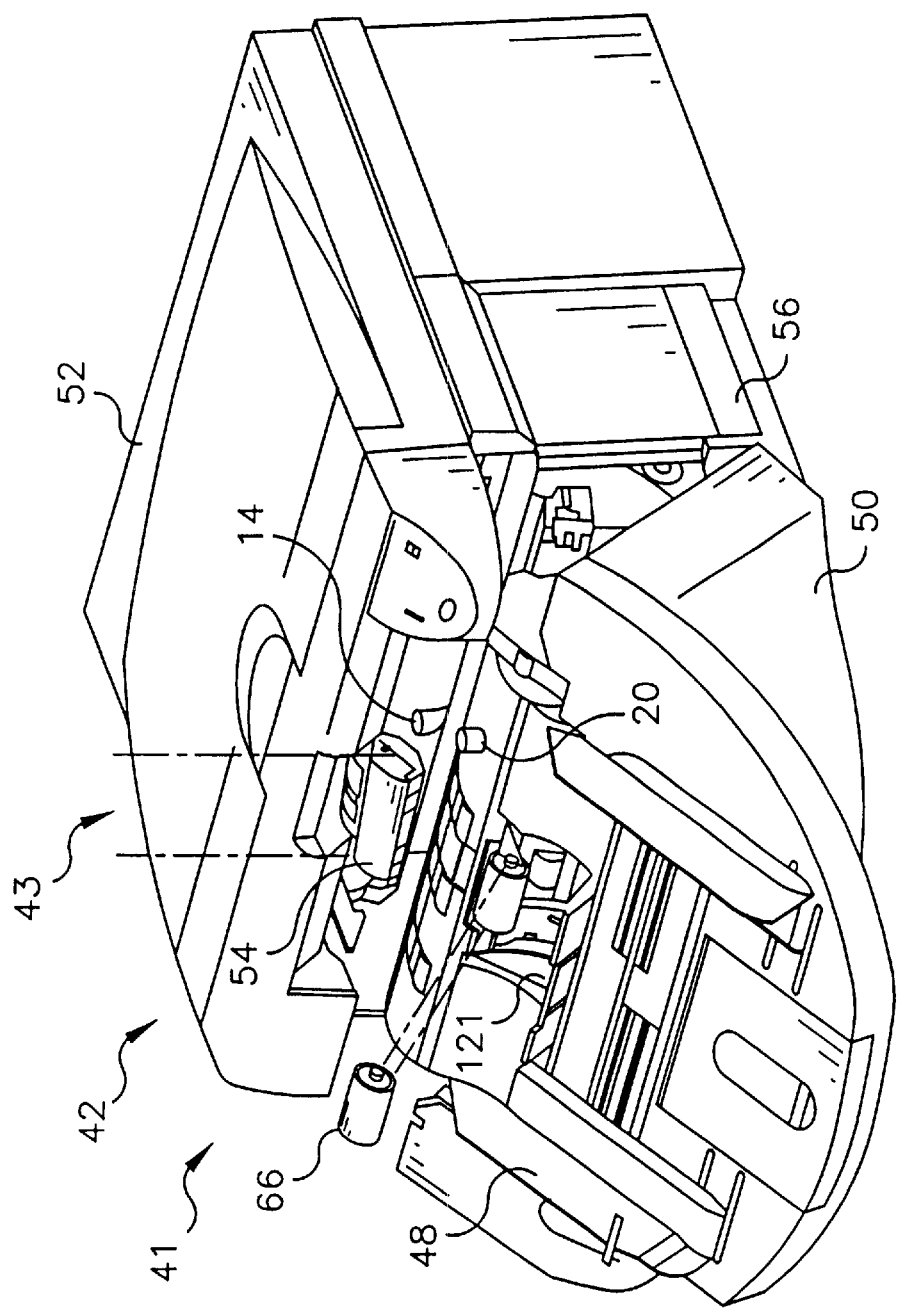
FIG. 2 is a perspective view of a [typical] sheet feeding device with an ultrasonic detection circuit in accordance with the present invention.

A typical device or apparatus 41 employing a document transport, in this case a sheet feeder, is shown in FIG. 2. The apparatus 41 includes a document processing system 43, a document transport system 42, and a multiple document detection system 10 as illustrated in FIG. 1. A variety of different types of document processing systems 43 can be used, such as scanning devices, copiers, and facsimile machines. Since the components and operation of document processing systems 43 are well know to those of ordinary skill in the art, they will not be discussed here.

In this particular embodiment, the document transport system 42 is a sheet feeding device which comprises a stack support 48 disposed in a first portion 50 of a housing 52 which also houses the document processing system 43 in this example. A feed module 54 is detachably mounted in a second portion 56 of the housing 52 so as to be in contact with a stack of documents. Separator 66 is a mechanical means for reducing multiple feeds. Ultrasonic transmitter 14 and ultrasonic receiver 20 are positioned so that documents for each document feed 18 are transported between them after the documents leave the stack. Other locations in the document transport system 42 may also be suitable for positioning the ultrasonic transmitter and receiver 14 and 20. Multiple documents in a document feed 18 which are not physically separated by separator 66 are detected by the multiple document detection system 10 as described above with reference to FIG. 1. Although one type of document transport system 42 is disclosed, other types of document transport systems 42 can also be used.

The invention has been described in detail with particular reference to certain preferred embodiments, but it will be understood that variations and modifications can be effected within the scope of the invention. For example, the microprocessor 32, described in the preferred embodiment, may be replaced with other types of processors, such as a simpler "and/or" gate or logic circuit which performs the same function described above.

PARTS LIST

10. Apparatus
11. Signaling system
12. Ultrasonic drive circuit
13. Drive signal
14. Ultrasonic transmitter
16. Ultrasonic signal
17. Ultrasonic signal
18. Document feed
20. Ultrasonic receiver
21. Electronic signal
22. Analyzer
23. Electrical signal
24. Phase comparator
26. Amplitude measurement circuit
28. Information signal
30. Information signal
32. Microprocessor
41. Apparatus
42. Document transport system
43. Document processing system
48. Stack support
50. First portion
52. Housing
54. Feed module
56. Second portion
66. Separator

What is claimed is:

1. An apparatus for multiple document detection comprising:
   a signaling system which transmits a signal to and receives the signal from a document feed, said document feed comprising one or more documents;
   an analyzer which determines if said document feed comprises two or more of the documents in response to a phase shift and an amplitude change between said transmitted signal and said received signal; and
   wherein said document feed comprises two or more of said documents if either said phase information signal or said amplitude information signal indicates two or more of said documents.

2. The apparatus for multiple document detection as in claim 1 wherein said signaling system comprises:
   a transmitter for transmitting said signal;
   a driver for driving the transmitter; and
   a receiver for receiving said signal.

3. The apparatus for multiple document detection as in claim 1 wherein said analyzer comprises:
   a phase comparator for comparing said transmitted signal and said received signal;
   an amplitude measurement circuit generating an amplitude information signal based on the comparison of said received signal to a second reference signal; and
   a processor determining if said document feed comprises two or more of said documents in response to a phase information signal and said amplitude information signal.

4. The apparatus for multiple document detection as in claim 3 wherein said document feed comprises two or more of said documents only if both said phase information signal and said amplitude information signal indicate two or more of said documents.

5. The apparatus for multiple document detection as in claim 3 wherein;
   said phase information signal is assigned a first weighting factor;
   said amplitude information signal is assigned a second weighting factor; and
   the processor determines if said document feed comprises two or more of said documents in response to said phase information signal taking into account said first weighting factor and said amplitude information signal taking into account said second weighting factor.

6. The apparatus for multiple document detection as in claim 1 wherein said signal is an ultrasonic signal.

7. A method for determining the presence of multiple documents comprising the steps of:
   transmitting a signal through a document feed comprising one or more documents;
   receiving said signal after it has passed through said document feed;
   comparing a phase of said transmitted signal and a phase of said received signal to provide a first information signal;
   comparing an amplitude of the transmitted signal and the received signal to provide a second information signal;
   analyzing said first and second information signals to determine if said document feed comprises two or more of said documents; and
   wherein said document feed comprises two or more of said documents if either said first information signal or said second information signal indicates two or more of said documents.

8. The method as set forth in claim 7 wherein the document feed comprises two or more of said documents only if both said first information signal and said second information signal indicate two or more of said documents.

9. The method as set forth in claim 7 further comprising applying a first weighting factor to said first information signal and applying a second weighting factor to said second information signal before analyzing said first and second information signals with said first and second weighting factors, respectively, to determine if said document feed comprises two or more of said documents.

10. The method as set forth in claim 7 wherein said signal is an ultrasonic signal.

11. An apparatus comprising:

a document processing system;

a document transport system which supplies at least one document feed to said document processing system, said document feed comprising one or more documents;

a multiple document detection system which determines if said document feed comprises two or more of said documents in response to a phase shift and an amplitude change between a signal transmitted to and received from said document feed; and wherein said document feed comprises two or more of said documents only if either said phase information signal or said amplitude information signal indicate two or more of said documents.

12. The apparatus as set forth in claim 11 wherein said multiple document detection system further comprises:

a transmitter for transmitting said signal;

a driver for driving said transmitter; and a receiver for receiving said signal.

13. The apparatus as set forth in claim 11 wherein said multiple document detection system further comprises;

a phase comparator for comparing the transmitted signal and the received signal;

an amplitude measurement circuit generating an amplitude information signal based on the comparison of said received signal to a second reference signal; and a processor determining if said document feed comprises two or more of said documents in response to a phase information signal and said amplitude information signal.

14. The apparatus as set forth in claim 13 wherein said document feed comprises two or more of said documents only if both said phase information signal and said amplitude information signal indicate two or more of said documents.

15. The apparatus as set forth in claim 13 wherein:

said phase information signal is assigned a first weighting factor;

said amplitude information signal is assigned a second weighting factor; and said processor determines if said document feed comprising two or more of said documents in response to said phase information signal taking into account said first weighting factor and said amplitude information signal taking into account said second weighting factor.

16. The apparatus as set forth in claim 11 wherein said signal is an ultrasonic signal.

17. The apparatus as set forth in claim 11 wherein said document processing system comprises a scanner system.

18. The apparatus as set forth in claim 11 wherein said document processing system comprises a facsimile system.

19. The apparatus as set forth in claim 11 wherein said document transport system comprises is a sheet feeder.

* * * * *

UNITED STATES PATENT AND TRADEMARK OFFICE
CERTIFICATE OF CORRECTION

PATENT NO.      : 6,511,064 B1
DATED           : January 28, 2003
INVENTOR(S)     : Daniel P. Phinney et al.

It is certified that error appears in the above-identified patent and that said Letters Patent is hereby corrected as shown below:

<u>Title page,</u>
Item [73], Assignee, add -- Rochester Institute of Technology, Rochester, NY (US) --

Signed and Sealed this

Twenty-seventh Day of May, 2003

JAMES E. ROGAN
*Director of the United States Patent and Trademark Office*